US005342345A

United States Patent [19]

Spencer

[11] Patent Number: 5,342,345

[45] Date of Patent: Aug. 30, 1994

[54] SOLUTION BAG WITH PLASTIC CONNECTING TUBE

[75] Inventor: Dudley W. C. Spencer, Wilmington, Del.

[73] Assignee: Denco, Inc., Wilmington, Del.

[21] Appl. No.: 95

[22] Filed: Jan. 4, 1993

[51] Int. Cl.[5] .......... A61M 5/00

[52] U.S. Cl. .......... 604/408; 604/403

[58] Field of Search .......... 604/403, 408, 411, 414, 604/415, 905

[56] References Cited

U.S. PATENT DOCUMENTS

| | | | |
|---|---|---|---|
| 3,276,447 | 10/1966 | Hamilton | 604/403 |
| 4,228,835 | 10/1980 | Robinson et al. | 604/408 |
| 4,369,779 | 1/1983 | Spencer | 604/408 X |
| 4,412,835 | 11/1983 | Spencer | 604/905 X |
| 4,828,557 | 5/1989 | Persidsky | 604/408 |
| 4,832,773 | 5/1989 | Shaposka et al. | 604/905 X |
| 5,004,113 | 4/1991 | Nogawa | 604/403 X |
| 5,224,937 | 7/1993 | Van der Heiden et al. | 604/905 X |

*Primary Examiner*—Robert A. Hafer
*Assistant Examiner*—Sam Rimell
*Attorney, Agent, or Firm*—Connolly & Hutz

[57] ABSTRACT

A solution bag for containing consumables is made of a plastic material which is closed around its edges and has a sealed access edge. A plastic discharge tube is mounted at the access edge and communicates with the interior of the bag. The tube is an elongated tube which would be connected at a dispensing site so that the contents may flow from the bag into the dispensing site. The tube has a terminal seal at its end remote from the access edge. The tube includes as a characteristic feature of the invention a safety seal located between the access edge and the terminal seal.

12 Claims, 1 Drawing Sheet

SOLUTION BAG WITH PLASTIC CONNECTING TUBE

BACKGROUND OF THE INVENTION

Solution bags are used for holding and/or dispensing various types of consumables, such as filters, membranes, assays, nutrients, innoculants, buffers, antibiotics, isotopes, hepatitis and AIDS indicators, samples etc. The solution bags include at least one tube mounted at an access edge so that each tube may communicate with the interior of the bag. One of the tubes is a pig-tail which is an elongated tube having a terminal seal at its end remote from the access edge of the solution bag. The pig-tailed tube would be located at a dispensing site where the terminal seal would be opened to permit the contents of the bag to be dispensed.

When such solution bags are steamed sterilized the bags are mounted within an outer seal bag. In conventional practices the pig-tail tube becomes saturated, opaque and severely softened. In practice the pig-tail tube would be welded to another tube section to create communication between the solution bag and, for example, a tube leading to a patient. The bag solution traverses up the pig-tail tube to the terminal end before the welding procedure. The difficulties that result from the pig-tail tube becoming saturated, opaque and severely softened reduce the weld strength by about 50%.

Similar problems exist for solution bags holding blood wherein the blood is removed from a plastic tube connected to the bag interior.

SUMMARY OF THE INVENTION

An object of this invention is to provide improvements in the plastic outlet tube of a solution bag which overcomes the above problems.

A further object of this invention is to provide such improvements which can be incorporated in the pig-tail or outlet tube during factory manufacture of the solution bags and before the solution is introduced into the bag.

In accordance with this invention a solution bag for containing consumables is made of a plastic material having closed edges including a sealed access edge. A pig-tail tube or an outlet communicates with the interior of the bag through the access edge. The tube includes a terminal seal at its end remote from the access edge. In accordance with the invention a safety seal is provided in the tube at a location between the access edge and the terminal seal.

The safety seal may be formed by utilizing a weld which is of sufficient strength to maintain the portion of the tube between the safety seal and the terminal seal in a dry condition and yet permit the safety seal to be easily reopened when desired so as to permit communication between the terminal end of the tube and the interior of the solution bag.

THE DRAWINGS

DETAILED DESCRIPTION

Figure 1:
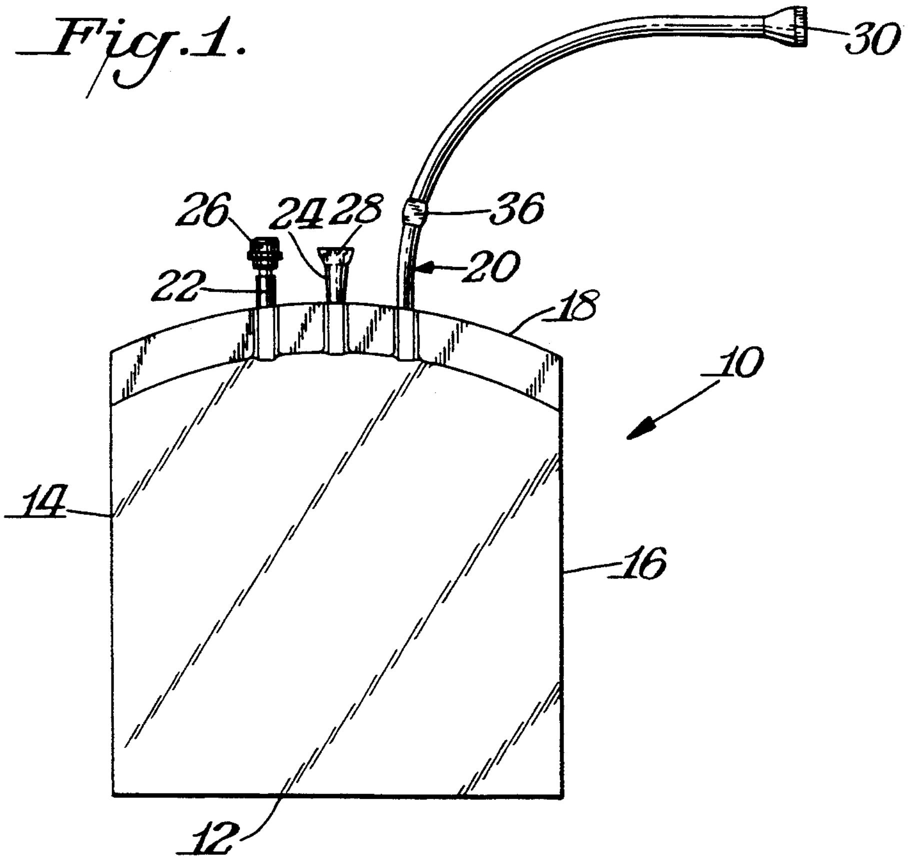
FIG. 1 is a front elevational view of a solution bag in accordance with this invention.

FIG. 1 illustrates a solution bag 10 in accordance with this invention. Solution bag 10 is made of conventional construction in that it includes sealed edges namely sealed side edges 14,16 joined by a sealed intermediate edge 12 and a sealed remote edge 18. Edge 18 may be considered an access edge since communication with the interior of bag 10 is accomplished by the provision of at least one outlet tube through access edge 18.

FIG. 1 illustrates a typical structure for the various types of tubes that would be mounted to access edge 18. One of the outlet tubes is an elongated pig-tail tube 20. Other possible tubes include tubes 22 and 24 for specific purposes. The specific number of tubes could vary in accordance with the intended use. Each tube would be sealed at its free end. For example, tube 22 may have a sealing plug 26 through which a hypodermic needle could be inserted to supply a consumable into the interior of bag 10. Tube 24 might also be used for the supply of consumables and might terminate in an edge 28 which is sealed after tube 24 has been used for insertion purposes. In conventional practices pig-tail tube 20 would have a terminal seal 30 at its end remote from access edge 18.

The above described structure is exemplary of conventional structure for solution bags. Such bags could be used in various applications, such as blood processing, CAPD-renal, plasma pherisis, fractionation, urinary drainage, bio-tech, hospital pharmacea, general bio & chem lab usage, chemo-therapy, TPN, IV solution additions. In such applications consumables including, for example, filters, membranes, assays, nutrients, innoculants, buffers, antibiotics, isotopes, hepatitis and AIDS indicators, and samples would be dispensed. It is to be understood that as used in this application the term "consumables" is meant to include the specifically indicated examples.

In use the terminal end of pig-tail tube 20 where terminal seal 30 is located would be connected at a dispensing site. For example, in kidney dialysis the solution bag 10 might be a dialysate bag which would be used to supply a dialysate to a patient. When the dialysate has been dispensed from the bag it is necessary to replace the bag with a new bag. Prior to the replacement with a new bag, the new bag would be steam sterilized. After sterilization the end of pig-tail tube 20 at terminal seal 30 would be welded to a tube located at the patient so as to connect the new dialysate bag to the patient.

Figure 2:
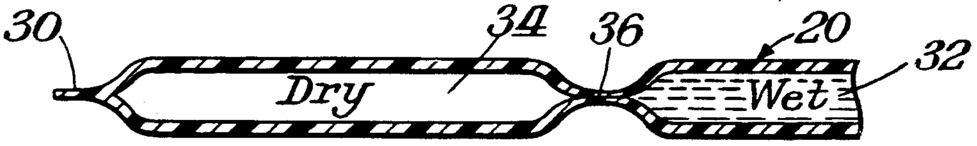
FIG. 2 is a cross-sectional view taken through the pig-tail tube of the solution bag of FIG. 1.

The present invention is intended to overcome disadvantages with conventional solution bags which tend to become water saturated, opaque and severely softened because of the tendency for the liquid solution in the bag to flow into the pig-tail tube 20 and be present throughout the pig-tail tube including the area near terminal seal 30. The present invention provides a safety seal 36 at a location between terminal seal 30 and access edge 18. As shown in FIG. 2 the provision of safety seal 36 prevents the liquid 32 from within solution bag 10 from flowing beyond safety seal 36. Thus, the interior 34 of pig-tail tube 20 is a dry chamber between the safety seal 36 and the terminal seal 30. As a result of chamber 34 being dry, the invention avoids soft, opaque, solution filled tubes. This assures that the welds are, for example, 75% of the original tube strength.

Safety seal 36 may be formed in any suitable manner. In the preferred practice of this invention total containment techniques may be used, such as disclosed in U.S. Pat. Nos. 4,793,880 and 4,753,697 and disclosed in pending application Ser. Nos. 764,249 filed Sep. 23, 1991 and 904,589 filed Jun. 26, 1992. The details of these patents and applications are incorporated herein by reference thereto. In general the total containment welding techniques involve heat sealing a plastic tube which can then be easily opened by a rolling or pressing action on the seal. As a result, the invention provides an extra safety seal 36 that the patient opens when the patient is satisfied that the main seal formed when the end of pig-tail tube 20 is welded to a further tube section is satisfactory. The safety seal 36 can be made during factory manufacture of the solution bags and before the solution is introduced into the bag to further assure that none of the solution 32 flows into the dry portion 34 of pig-tail tube 20.

In a practice of this invention the length of pig-tail tube 20 having the dry chamber 34 might be, for example, 6 cm. long between terminal seal 30 and safety seal 36. The flange resulting at terminal seal 30 might be 1 mm while the thickness of tube 20 between the flange and the interior chamber 34 might also be 1 mm. By forming safety seal 36 as an integral seal the user is provided with a positively closed safety seal before opening the infusion line. This would be more reliable than the use of external clamps. The invention provides an overall sterility and total containment performance improvement. Safety seal 36 would be opened after the terminal end of tube 20 is welded.

Figure 3:
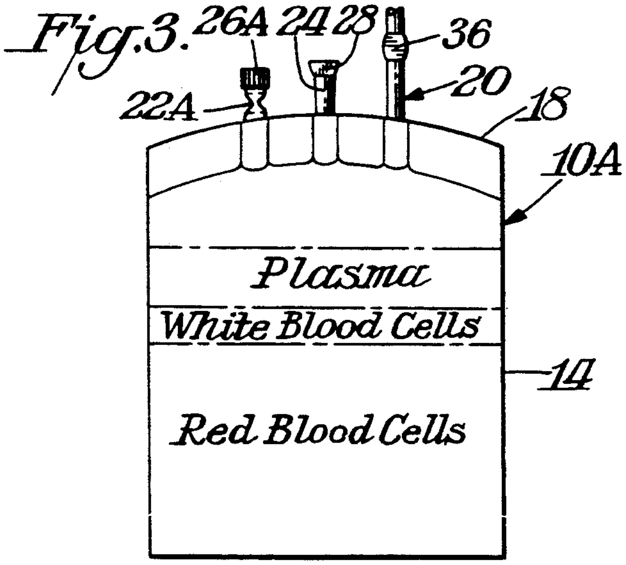
FIG. 3 is a front elevational view of a solution bag similar to the solution bag of FIG. 1, but specifically used for blood samples.
Figure 4:
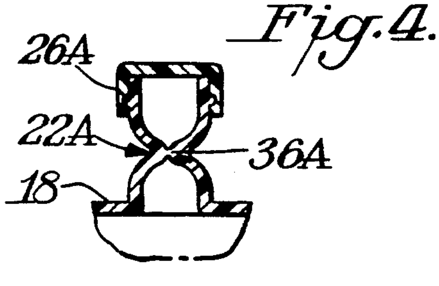
FIG. 4 is an enlarged cross-sectional view in elevation showing the safety seal for the outlet tube of the solution bag in FIG. 3.

FIG. 3 shows the use of the invention for a solution bag 10A used in connection with blood processing. As shown therein the solution bag 14 has the blood arranged in layers of red blood cells at the bottom and plasma at the top with the white blood cells therebetween. Solution bag 10A could be provided with any number of outlet tubes. For the sake of illustration three tubes, 22A, 24 and 20 are illustrated. When used for obtaining blood from solution bag 10A in the illustrated embodiment, outlet tube 22A would be used. As better shown in FIG. 4, outlet tube 22A includes a cap or other closure 26A which is snapped onto the free end of tube 22A. In accordance with this invention, a safety seal 36A is provided between the access edge 18 and the free end having cap 26A. Safety seal 36A could be formed in the same manner as safety seal 36 by welding the tube together as previously described. A rolling action or other pressure could then pop discharge tube 22A open when it is desired to withdrawn blood from discharge tube 22A.

Figure 5:
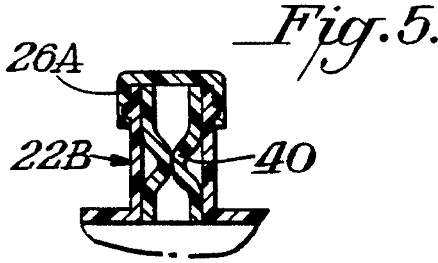
FIG. 5 is a view similar to FIG. 4 showing an alternative form of safety seal in accordance with this invention.

FIG. 5 illustrates an alternative practice of the invention wherein discharge tube 22B has a cap 26A at its free end and the safety seal is formed by a separate closure member 40 inserted in discharge tube 22B. Closure member 40 may take any suitable form and could, for example, be a plastic tube section tightly fitted into discharge tube 22B so that communication between the upstream and downstream portions of discharge tube 22B is opened by breaking the seal formed by safety seal 40. Any other suitable valve member may be used in accordance with this invention. What is necessary is that the valve member provide a temporary closure preventing flow of blood completely through outlet tube 22B until the seal formed by the valve member is broken. Once the safety seal 36A or 40 is broken to permit communication it is not necessary to again utilize the safety seal for closing the flow through the discharge tube. Accordingly, the valve member 40 could be of single use structure. Similarly, safety seal 36 would not be resealed once the seal is broken.

It is to be understood that although the provision of a safety seal for an outlet tube of a solution bag has been described specifically with regard to the elongated pig-tail and with regard to a single discharge tube. Any number of tubes may be utilized for the solution bag with any number of the tubes including a safety seal.

What is claimed is:

1. In a solution bag for containing consumables, said bag being made of a plastic material having closed peripheral edges including an access edge, an elongated plastic discharge tube mounted to said access edge and communicating with the interior of said bag whereby the contents of said bag may flow through said discharge tube to a dispensing site, said discharge tube having a terminal end remote from said access edge, said terminal end having a terminal seal to close said discharge tube, the improvement being in that said discharge tube includes a safety seal at a location between said access edge of said bag and said terminal seal to prevent flow of the consumable completely through said discharge tube until the seal of said safety seal is broken, said safety seal being formed by welding said tube closed at said location of said safety seal, said safety seal being integral with said discharge tube, and said safety seal being openable under external finger pressure.

2. The solution bag of claim 1 including a liquid solution in said bag, said liquid solution being flowable from said bag into said discharge tube up to said safety seal, and the portion of said discharge tube between said safety seal and said terminal seal comprising a dry chamber.

3. The solution bag of claim 2 including at least one further plastic tube mounted to said access edge for the introduction of a consumable into said bag.

4. The solution bag of claim 2 wherein said solution is a consumable.

5. The solution bag of claim 2 wherein said solution is a blood sample.

6. The solution bag of claim 2 wherein said discharge tube is a pig-tail tube.

7. A method of providing a consumable at a dispensing site including the steps of providing a solution bag containing the consumable with the solution bag having sealed edges including an access edge with a pig-tail tube communicating with the interior of the bag through the access edge, forming a heat welded safety seal in the pig-tail tube at a location between the remote end of the pig-tail tube and the access edge with the safety seal being openable under external finger pressure, permitting flow communication of the consumable in the pig-tail tube from the solution bag to the safety seal and preventing flow downstream from the safety seal, forming a terminal seal at the end of the tube remote from the access edge, creating a dry chamber between the safety seal and the terminal seal, connecting the pig-tail tube at the dispensing site by welding the end of the pig-tail tube having the terminal seal to a further plastic tube, opening the seal resulting from welding the pig-tail tube to the further plastic tube, opening the safety seal to permit the consumable to flow downstream of the safety seal, and discharging the consumable through the pig-tail tube to flow through the further tube at the dispensing site.

8. The method of claim 7 including the forming of the safety seal by welding a portion of the pig-tail tube to itself, and opening the safety seal by applying pressure to the safety seal.

9. The method of claim 8 wherein the consumable is a dialysate and including the steps of removing a used dialysate bag from connection to a patient, and welding the solution bag as a new dialysate bag to the further plastic tube leading from the patient.

10. In a method of providing a blood sample including the steps of providing a solution bag containing blood with the solution bag having sealed edges including an access edge with a plastic discharge tube communicating with the interior of the bag through the access edge, forming a heat welded safety seal in the discharge tube at a location between the remote end of the discharge tube and the access edge with the safety seal being openable under external finger pressure, permitting flow communication of the blood in the discharge tube from solution bag to the safety seal and preventing flow downstream from the safety seal, forming a terminal seal at the end of the discharge tube remote from the access edge, creating a dry chamber between the safety seal and the terminal seal, opening the safety seal to permit the blood to flow downstream of the safety seal, unsealing the terminal seal, and flowing the blood from the solution bag into the discharge tube past the opened safety seal and out of the discharge tube through the unsealed terminal seal.

11. The method claim 10 including forming the safety seal by welding a portion of the discharge tube to itself, and opening the safety seal by applying pressure to the safety seal.

12. The method of claim 10 including forming the safety seal by inserting a separate valve closure member in the discharge tube.

* * * * *